(12) United States Patent
Ito et al.

(10) Patent No.: US 7,557,509 B2
(45) Date of Patent: Jul. 7, 2009

(54) GAS DISCHARGE TUBE LIGHT SOURCE APPARATUS AND LIQUID CHROMATOGRAPH

(75) Inventors: Yoshinobu Ito, Hamamatsu (JP); Masaki Ito, Hamamatsu (JP); Koji Matsushita, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 481 days.

(21) Appl. No.: 10/574,514

(22) PCT Filed: Dec. 12, 2005

(86) PCT No.: PCT/JP2005/022790

§ 371 (c)(1),
(2), (4) Date: Apr. 3, 2006

(87) PCT Pub. No.: WO2007/004319

PCT Pub. Date: Jan. 11, 2007

(65) Prior Publication Data

US 2008/0246400 A1   Oct. 9, 2008

(30) Foreign Application Priority Data

Jun. 30, 2005   (JP) .............................. 2005-192610

(51) Int. Cl.
*H01J 17/02* (2006.01)
(52) U.S. Cl. .................. 313/609; 313/613; 313/631
(58) Field of Classification Search ......... 313/627–643, 313/567, 111–117, 25–27, 318.01–318.09, 313/609–619; 439/615, 739; 445/24, 26, 445/22, 29
See application file for complete search history.

(56) References Cited

U.S. PATENT DOCUMENTS 4,611,143 A * 9/1986 Shimazu et al. ............. 313/111

(Continued)

FOREIGN PATENT DOCUMENTS

DE   WO 2004 051698 A2 * 6/2004

(Continued)

*Primary Examiner*—Peter J Macchiarolo
*Assistant Examiner*—Donald L Raleigh
(74) *Attorney, Agent, or Firm*—Drinker Biddle & Reath LLP

(57) ABSTRACT

The present invention relates to a gas discharge tube or the like having a structure for enabling the maintenance of discharge startability and the prevention of the shortening of the life of an anode section and for increasing the amount of visible light from a visible light source passing through a discharge path restricting section. The gas discharge tube comprises a sealed vessel in which gas is encapsulated. A cathode section and anode section for generating discharge are arranged in the sealed vessel. Furthermore, a discharge path restricting section for narrowing a discharge path is arranged between the cathode section and the anode section. In particular, an opening portion is formed in the anode section, and the cross section of the opening portion has a non-circular shape where the maximum opening width in a first direction is different from that in a second direction orthogonal to the first direction. Thus, the amount of the visible light passing through the opening portion of the anode section in the gas discharge tube from the visible light source can be increased by making the maximum opening width in one direction of the first and second directions longer than that in the other direction. The maintenance of the discharge startability and the prevention of the shortening of the life of the anode section can be attained by making the maximum opening width in the other direction shorter than that in one direction.

10 Claims, 17 Drawing Sheets

U.S. PATENT DOCUMENTS 4,622,485 A * 11/1986 Miyashita et al. ............. 313/25
7,397,190 B2 * 7/2008 Derra et al. ................. 313/618

FOREIGN PATENT DOCUMENTS

| | | |
|---|---|---|
| JP | 59-215654 | 12/1984 |
| JP | 05-109389 | 4/1993 |
| JP | 2001-035238 | 2/2001 |
| JP | 2001-256922 | 9/2001 |
| JP | 2001-256924 | 9/2001 |

* cited by examiner

GAS DISCHARGE TUBE LIGHT SOURCE APPARATUS AND LIQUID CHROMATOGRAPH

TECHNICAL FIELD

The present invention relates to a gas discharge tube for generating discharge for obtaining emitting light in a sealed vessel in which gas is encapsulated, a light source apparatus, and a liquid chromatograph.

BACKGROUND ART

For example, a light source apparatus, employed as a light source of a liquid chromatograph, a semiconductor inspection device, or the like, comprises at least a gas discharge tube for emitting light having a prescribed wavelength, and a visible light source arranged at the rear side of the gas discharge tube and emitting visible light to the gas discharge tube. The gas discharge tube used for the light source apparatus comprises a cathode section and anode section for generating the discharge. A circular opening for passing through the visible light from the visible light source is formed in the anode section. The circular opening provided in the anode section is arranged at a position where the visible light passing through the circular opening can pass through a discharge narrowing hole (discharge path restricting section) for narrowing a discharge path between the anode section and the cathode section (For example, refer to Patent Documents 1 and 2).

Patent Document 1: Japanese Patent Application Laid-Open No. S59-215654

Patent Document 2: Japanese Patent Application Laid-Open No. H5-109389

Patent Document 3: Japanese Patent Application Laid-Open No. 2001-35238

DISCLOSURE OF THE INVENTION

Problem to be Solved by the Invention

The present inventors have examined the above prior art, and as a result, have discovered the following problems. That is, when increasing the amount of light from the visible light source passing through the discharge narrowing hole in the conventional gas discharge tube, it is necessary to set the diameter of the circular opening of the anode section to be higher than the diameter of the discharge narrowing hole. However, a distance between the discharge narrowing hole and the opening edge part of the anode section becomes long in this case, and the discharge startability is reduced. In addition, since the area of the anode section is also reduced (the ratio of the opening area is larger based on the surface of the anode section), the temperature of the anode section is easily raised. As a result, the conventional gas discharge tube had a problem that the consumption of the anode section is accelerated (the shortening of the life of the gas discharge tube).

The present invention has been developed to eliminate the problems described above. It is an object of the present invention to provide a gas discharge tube having a structure realizing both the maintenance of discharge startability and the prevention of the shortening of the life of the anode section and capable of increasing the amount of the visible light from the visible light source passing through the discharge path restricting section, a light source apparatus, and liquid chromatograph.

Means for Solving Problem

A gas discharge tube according to the present invention comprises a sealed vessel in which gas is encapsulated, and a cathode section, an anode section and a discharge path restricting section are respectively arranged in the sealed vessel. The cathode section is an electrode for generating thermoelectrons contributing to discharge. The anode section is an electrode for receiving the thermoelectrons from the cathode section. Discharge is generated between the cathode section and the anode section. The discharge path restricting section functions to narrow a discharge path between the cathode section and the anode section. In particular, in the gas discharge tube according to the present invention, the anode section has a first surface facing the discharge path restricting section and a second surface opposing the first surface, and an opening portion for communicating between the first surface and the second surface. In the gas discharge tube, the cross section (defined on a reference plane made coincident with the first surface) of the opening portion has a non-circular shape.

A light source apparatus according to the present invention comprises the gas discharge tube (the gas discharge tube according to the present invention) having the above structure, and a visible light source for emitting visible light toward the opening portion of the anode section of the gas discharge tube. Furthermore, a liquid chromatograph according to the present invention includes the above light source apparatus.

In accordance with the gas discharge tube, light source apparatus and liquid chromatograph having the above structure, the cross section of the opening portion formed in the anode section has a non-circular shape. Therefore, for example, an opening width (opening length L) along a tube axial direction of the sealed vessel is made longer than the diameter of the circular opening (hereinafter, referred to as conventional circular opening) of an anode section in the conventional gas discharge tube. On the other hand, an opening width (opening width W) along a direction orthogonal to the tube axial direction of the sealed vessel can be made coincident with the diameter of the conventional circular opening portion. Thus, the amount of the visible light (supplied from the visible light source arranged on the rear side of the gas discharge tube) passing through the opening portion of the anode section in the gas discharge tube can be increased by making the opening length L longer than the diameter of the conventional circular opening. On the other hand, both the maintenance of the discharge startability and the prevention of the shortening of the life of the anode section can be realized by making coincident the opening width W with the diameter of the conventional circular opening. Herein, the term "non-circular shape" includes an oblong shape, an elliptic shape, a rectangular shape, a square shape, a rhomboid shape, a parallelogram shape, other polygon shape and the combination thereof. In other words, referring to the term "opening portion," the cross-sectional shape viewed from a direction extending along the optical axis X of the light emitted from the gas discharge tube should be the above shape. Herein, the term "opening length L" means a distance (opening width defined by straight distance) between the edge parts of the anode section defining the opening portion in a surface perpendicular to the optical axis X. The term "opening width W" means a line segment passing through the axial center of the opening portion and mutually orthogonally crossing among the line segments showing them. "The opening length L" is longer than "the opening width W."

More specifically, the cross section of the opening portion in the anode section can mean a non-circular shape where the maximum opening width in a first direction, is different from that in a second direction orthogonal to the first direction. Herein, when the first direction is made coincident with the tube axial direction of the sealed vessel, the maximum opening width in the first direction corresponds to the opening length L, and the opening width in the second direction corresponds to the opening width W. At this time, the opening length L can be made longer than the diameter of the conventional circular opening based on the diameter of the conventional circular opening, and the opening width W can be made coincident with the diameter of the conventional circular opening. The term "diameter" means a distance (opening width defined by straight distance) between the edge parts of the opening portion viewed from the direction extending along the optical axis of the light emitted from the conventional gas discharge tube, and a line segment passing through the axial center of the opening portion among the line segments showing them.

It is preferable that the cross section of the opening portion has one of the oblong shape, the elliptic shape and the rectangular shape, in the gas discharge tube according to the present invention. In addition to the above shapes, the cross section of the opening portion may have a shape for which the opening width of a part in the opening portion is adjusted by a projection extending along the reference plane from the edge part of the anode section defining the opening portion. Particularly, when the opening width (opening width W) in the second direction is limited, referring to the cross section of the opening portion, the maximum opening width in the second direction in the opening portion is adjusted by a projection extending in the second direction from the edge part of the anode section defining the opening portion. The increase of the opening area of the opening portion can be suppressed in either cross-sectional shape, and the opening width of a predetermined direction can be made larger than the diameter of the conventional circular opening. Therefore, as compared with the case where the opening area of the conventional circular opening is simply enlarged, the discharge startability can be enhanced by the increase of current capacity. Since the thermal capacity of the anode section is also increased in the same comparison, the life characteristic of the anode section can be enhanced. Herein, the term "oblong shape" means a shape defined by providing mutually parallel linear portions extending along a predetermined direction in the edge part of the anode section defining the opening portion. That is, when these linear parts (parallel part) extend along the first direction, the opening width between the linear parts is the opening width W. The edge part connecting the end parts of the linear parts may be any of a straight line and a curve (for example, circular).

The gas discharge tube according to the present invention may be a side-on type gas discharge tube for emitting light in a direction orthogonal to the tube axial direction of the sealed vessel. In this case, a first surface of the anode section is disposed so as to be parallel to the tube axial direction Y of the sealed vessel. That is, when the anode section is disposed so that the opening length L (the opening width of the longer width) in the opening portion extends along the tube axial direction Y, there is little influence on the discharge startability and the shortening of the life of the anode section even when the opening portion is misaligned to some degree in the tube axial direction Y to the discharge path restricting section.

On the contrary, the opening portion of the anode section and the discharge path restricting section are easily positioned, and the assembly efficiency of the gas discharge tube can be enhanced. Herein, the phase "the opening length L extends along the tube axial direction" means that the direction of the opening length is almost equal to that of the tube axis.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

Effect of the Invention

In accordance with the gas discharge tube, light source apparatus and liquid chromatograph according to the present invention, both the maintenance of the discharge startability and the prevention of the shortening of the life of the anode section can be realized, and the amount of the visible light from the visible light source passing through the discharge path restricting section can be increased.

DESCRIPTION OF THE REFERENCE NUMERALS

10 . . . gas discharge tube; 11 . . . sealed vessel; 12, 32, 33, 34, 35 . . . anode section; 12a . . . oblong opening; 13 . . . cathode section; 26 . . . discharge path restricting section; 26a . . . discharge path narrowing hole; 32a . . . elliptic opening; 36a . . . rectangular opening; 40 . . . light source apparatus; 85 . . . tungsten lamp (visible light source); 100 . . . liquid chromatograph; D1, D5, D7, D9, D11 . . . short width (maximum opening width of second direction: opening width); D2, D6, D8, D10, D12 . . . long width (maximum opening width of first direction: opening length); and Y . . . tube axial direction.

BEST MODES FOR CARRYING OUT THE INVENTION

Figure 7:
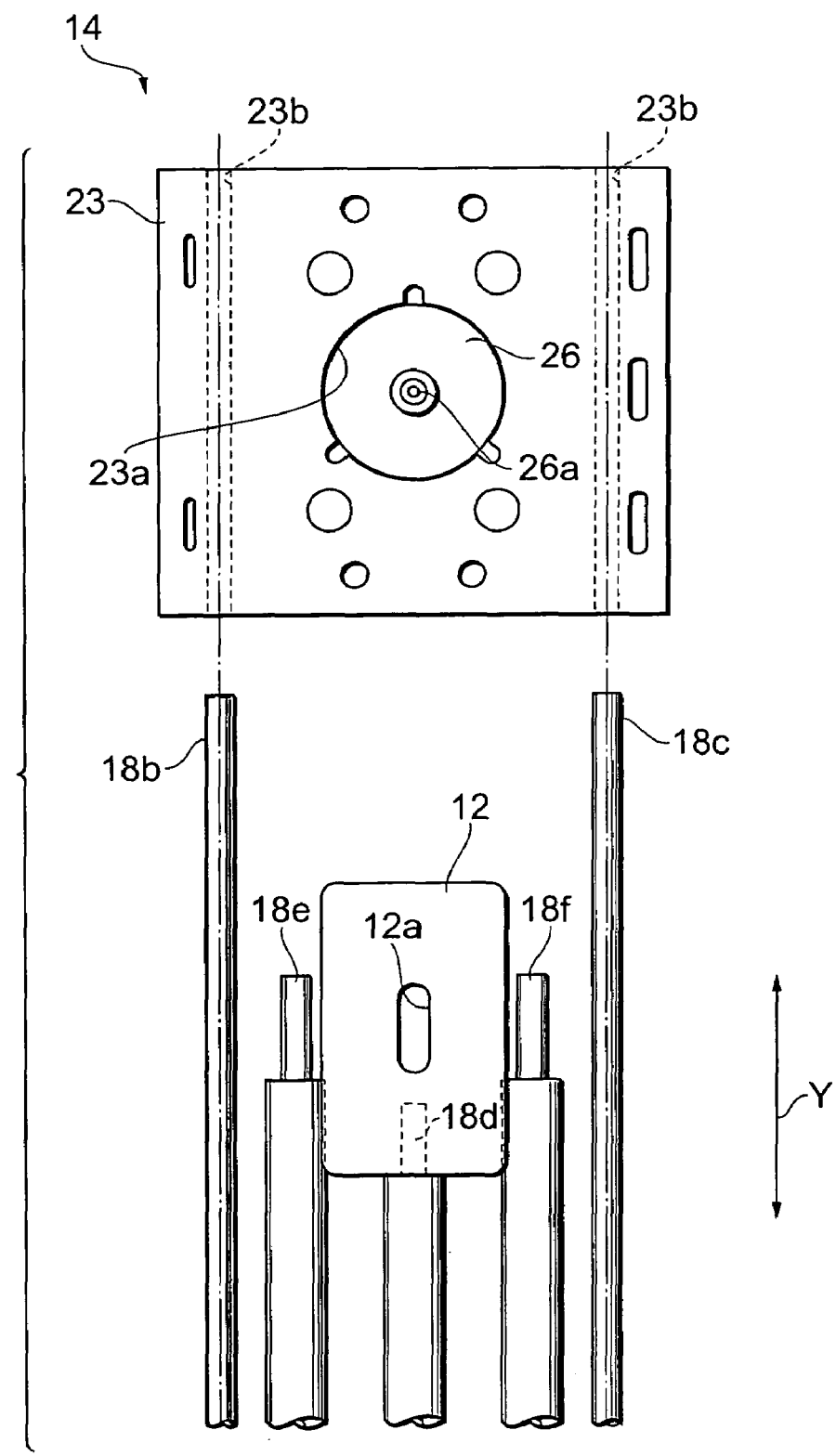
FIG. 7 is an exploded front view of the supporting part, discharge path restricting section and anode section in the light-emitting part assembly shown in FIG. 4.
Figure 8:
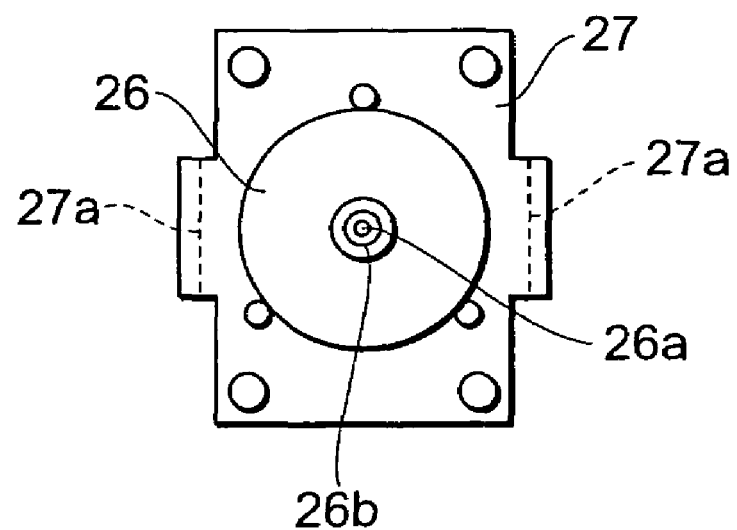
FIG. 8 is a front view of the discharge path restricting section and conductive plate in the light-emitting part assembly shown in FIG. 4.
Figure 9:
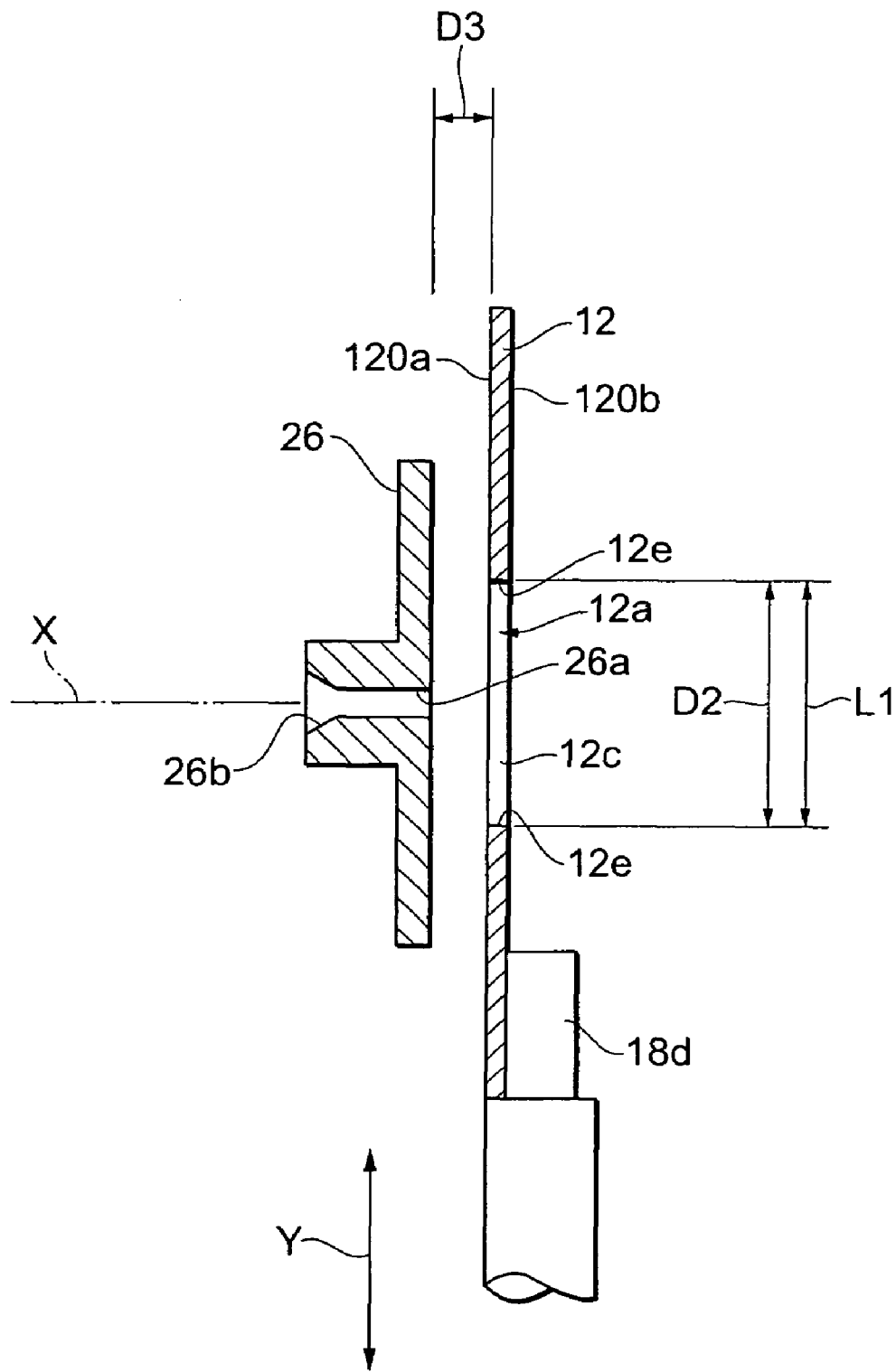
FIG. 9 is a longitudinal sectional view showing the positional relationship between a discharge path narrowing hole and opening portion (oblong shape) shown in FIG. 4.
Figure 10:
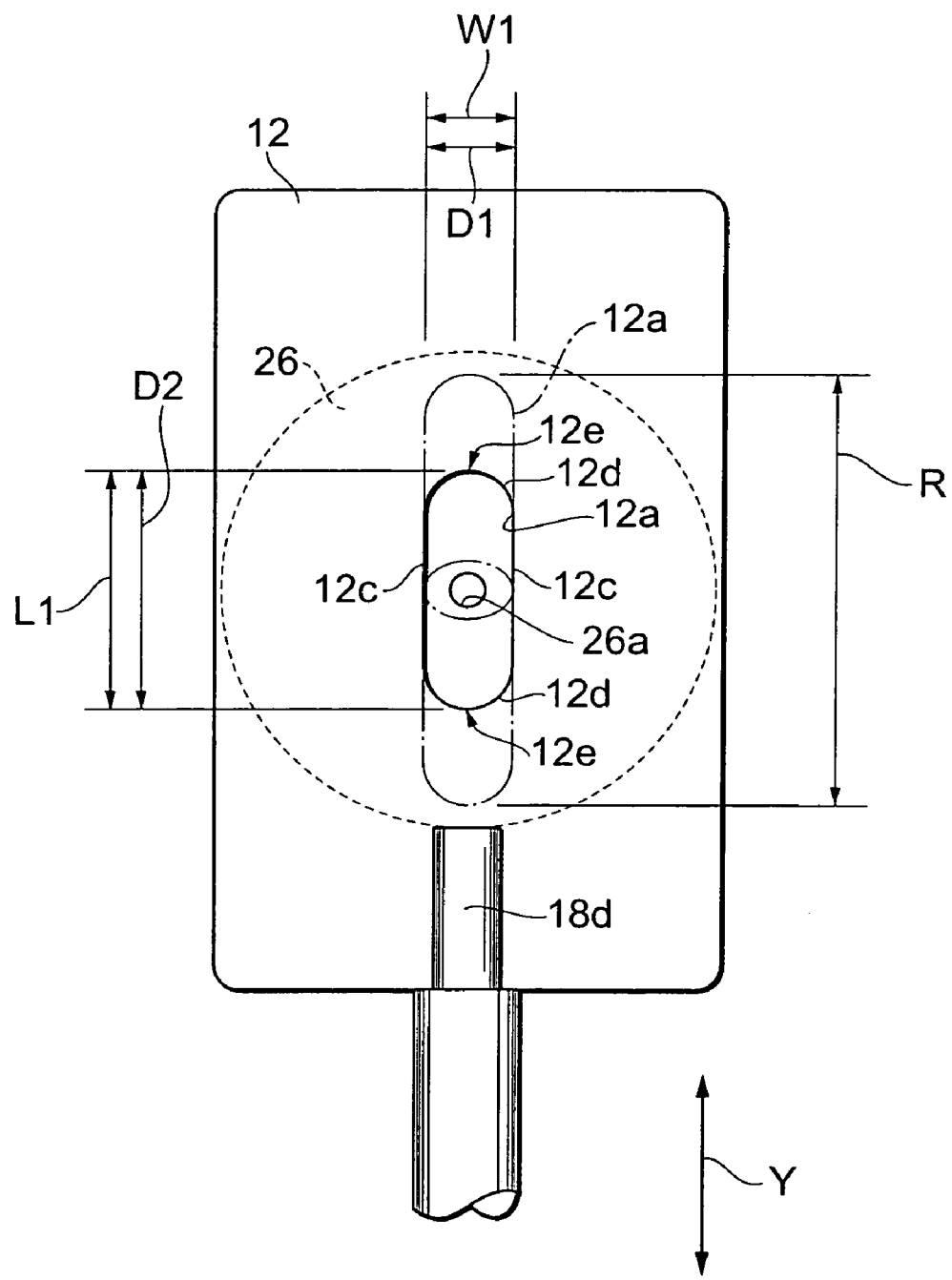
FIG. 10 is a rear view showing the positional relationship between the discharge path narrowing hole and opening portion (oblong shape) shown in FIG. 4.

In the following, embodiments of the present invention will be explained in detail using the drawings of the seventeen figures of the gas discharge tube, light source apparatus and liquid chromatograph according to the present invention. In the description of the drawings, identical or corresponding components are designated by the same reference numerals, and overlapping description is omitted. FIGS. 1 to 4 show an embodiment of a gas discharge tube according to the present invention. FIGS. 5 to 8 show a light-emitting part assembly shown in FIG. 4. FIGS. 9 and 10 show the positional relationship of a discharge path narrowing hole and oblong opening shown in FIG. 4. In the following description, the traveling direction of the emitted light is defined as "forward," and terms showing directions such as "before," "after," "front" and "rear" are used. Terms showing directions such as "upper" and "lower" are used in a state of each figure.

Figure 2:
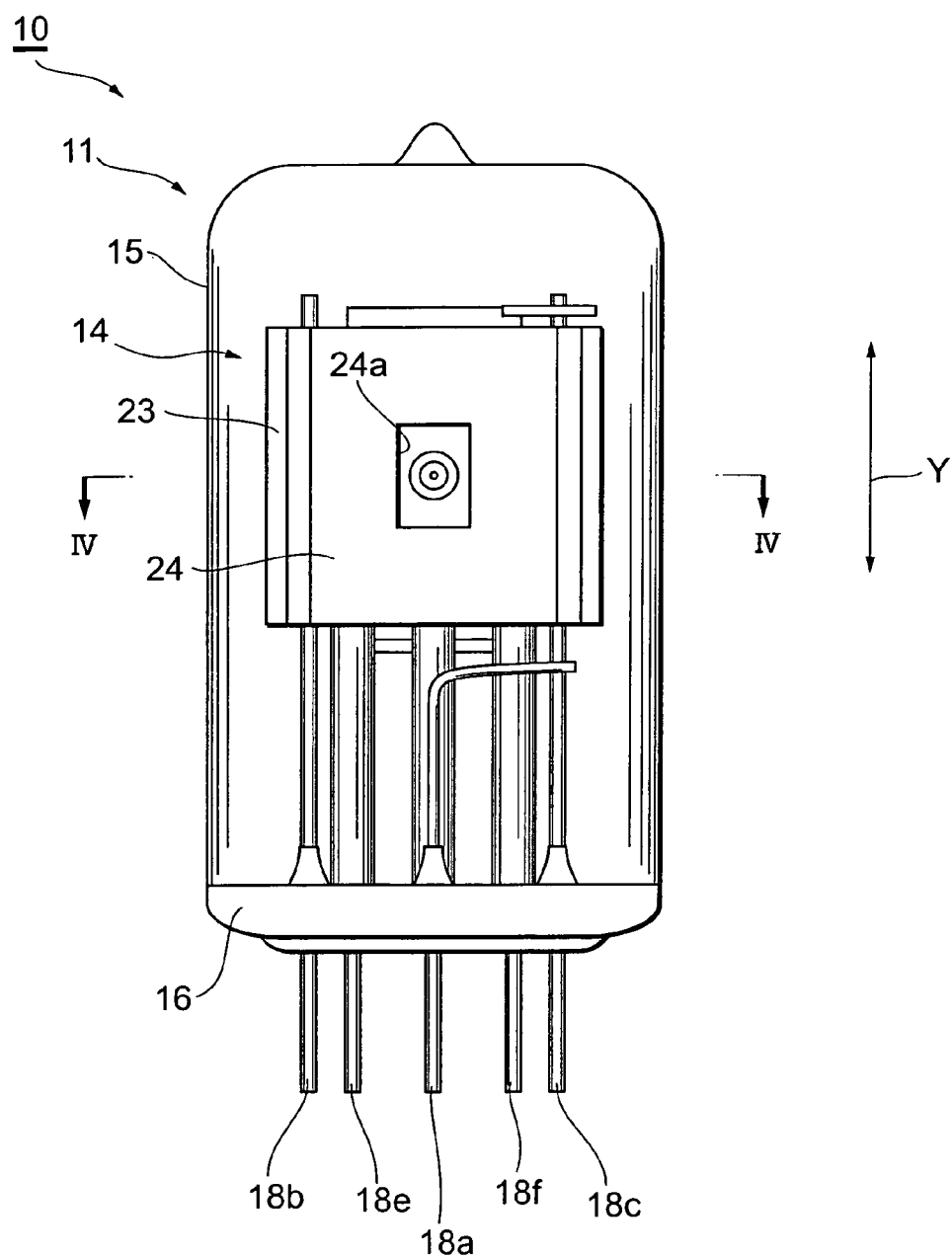
FIG. 2 is a front view of the gas discharge tube shown in FIG. 1.
Figure 3:
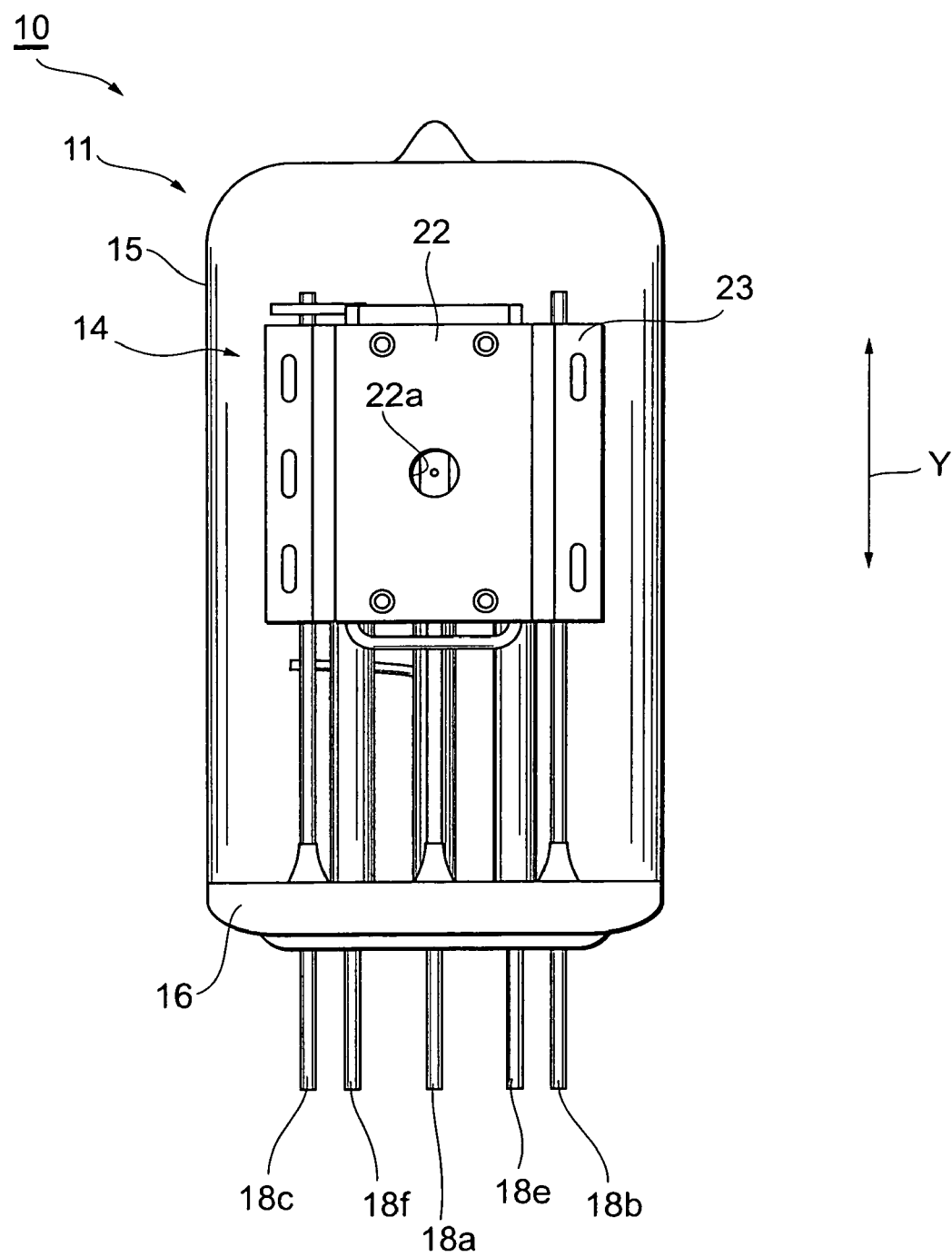
FIG. 3 is a rear view of the gas discharge tube shown in FIG. 1.
Figure 4:
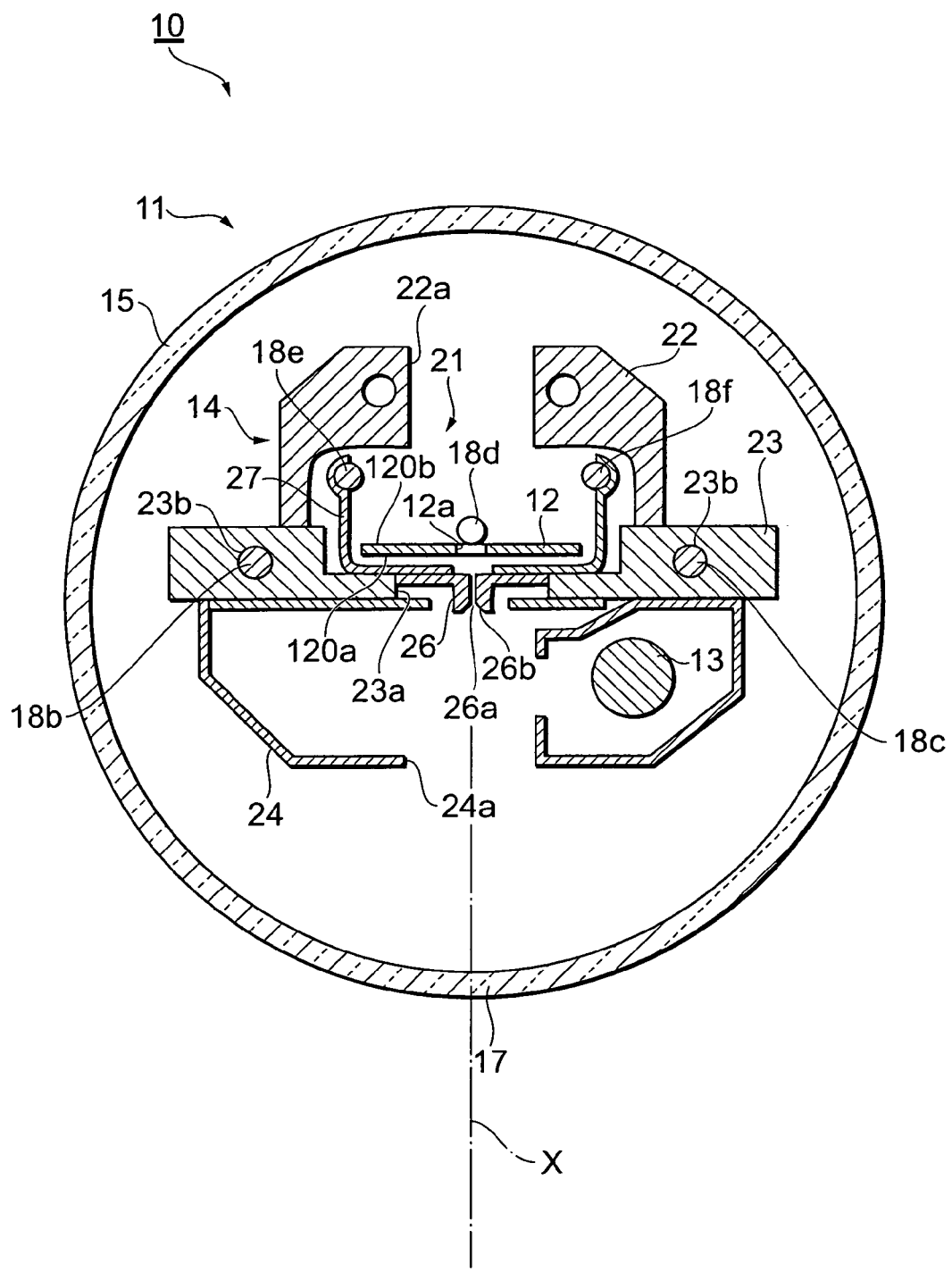
FIG. 4 is a sectional view of the gas discharge tube according to the first embodiment along IV-IV line in FIG. 2.

A gas discharge tube 10 shown in FIGS. 1 to 4 is a side-on type deuterium lamp for emitting ultraviolet radiation (200 to 400 nm) perpendicularly to a tube axial direction Y, and is also a see-through type gas discharge tube capable of passing through another light from the rearward. The gas discharge tube 10 can apply light emitted from another light source arranged on the rearward of the gas discharge tube 10 to an object arranged on the forward of the gas discharge tube 10. For example, the gas discharge tube 10 is used as a light source such as an analytical instrument and a semiconductor inspection device. The gas discharge tube 10 comprises a glass sealed vessel 11 in which deuterium gas of several hundred Pa is encapsulated. As shown in FIG. 4, a light-emitting part assembly 14 having an anode section 12 and a cathode section 13 and emitting ultraviolet radiation is housed in the sealed vessel 11.

Figure 1:
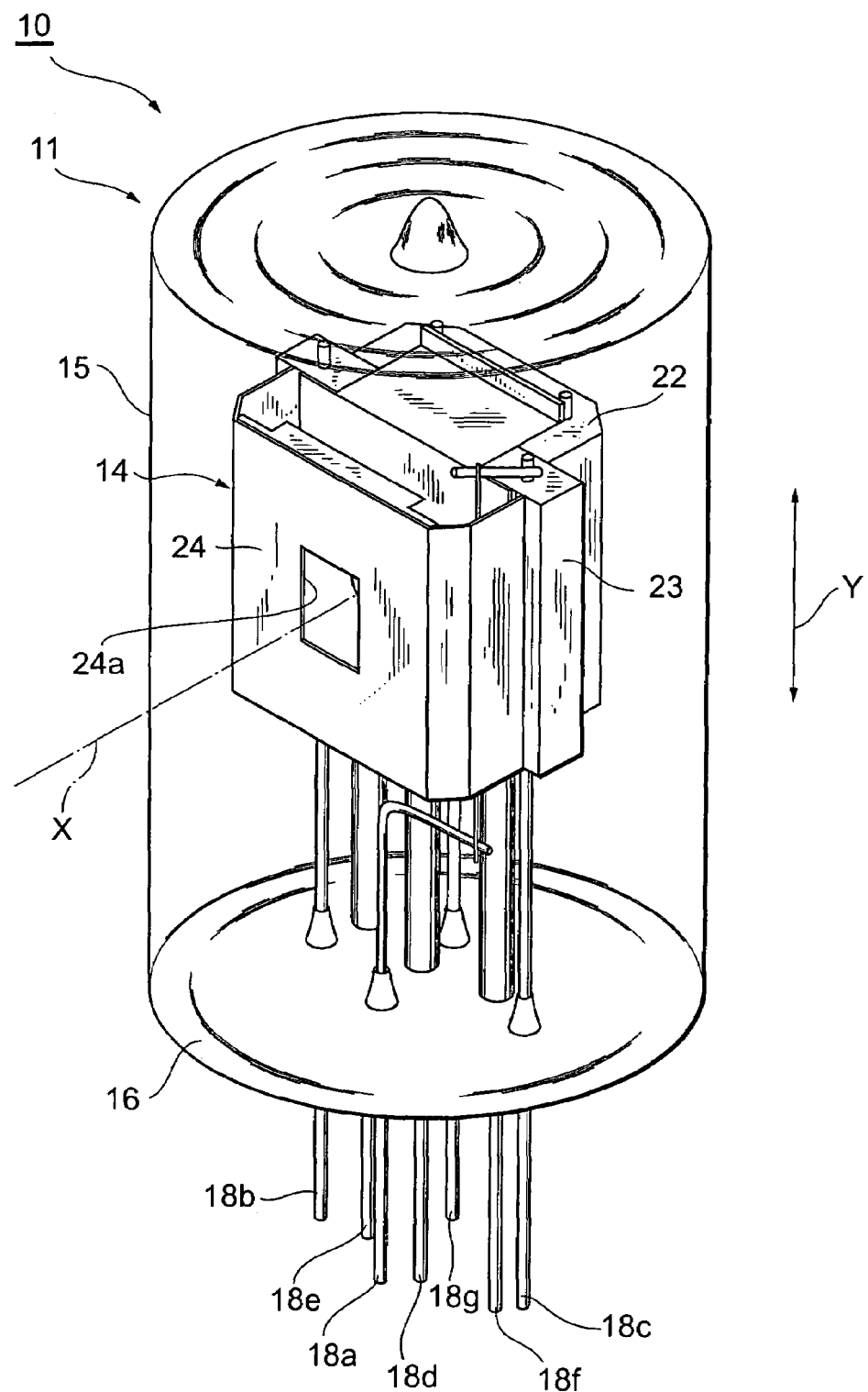
FIG. 1 is a perspective view showing the structure of an embodiment of a gas discharge tube according to the present invention.

As shown in FIGS. 1 to 3, the sealed vessel 11 is constituted by a cylindrical side tube part 15 of which one end (shown top end) side is sealed, and a stem part 16 for sealing the other end side of the side tube part 15. A part of the side tube part 15 is used as a light emitting window 17 (see FIG. 4).

Figure 5:
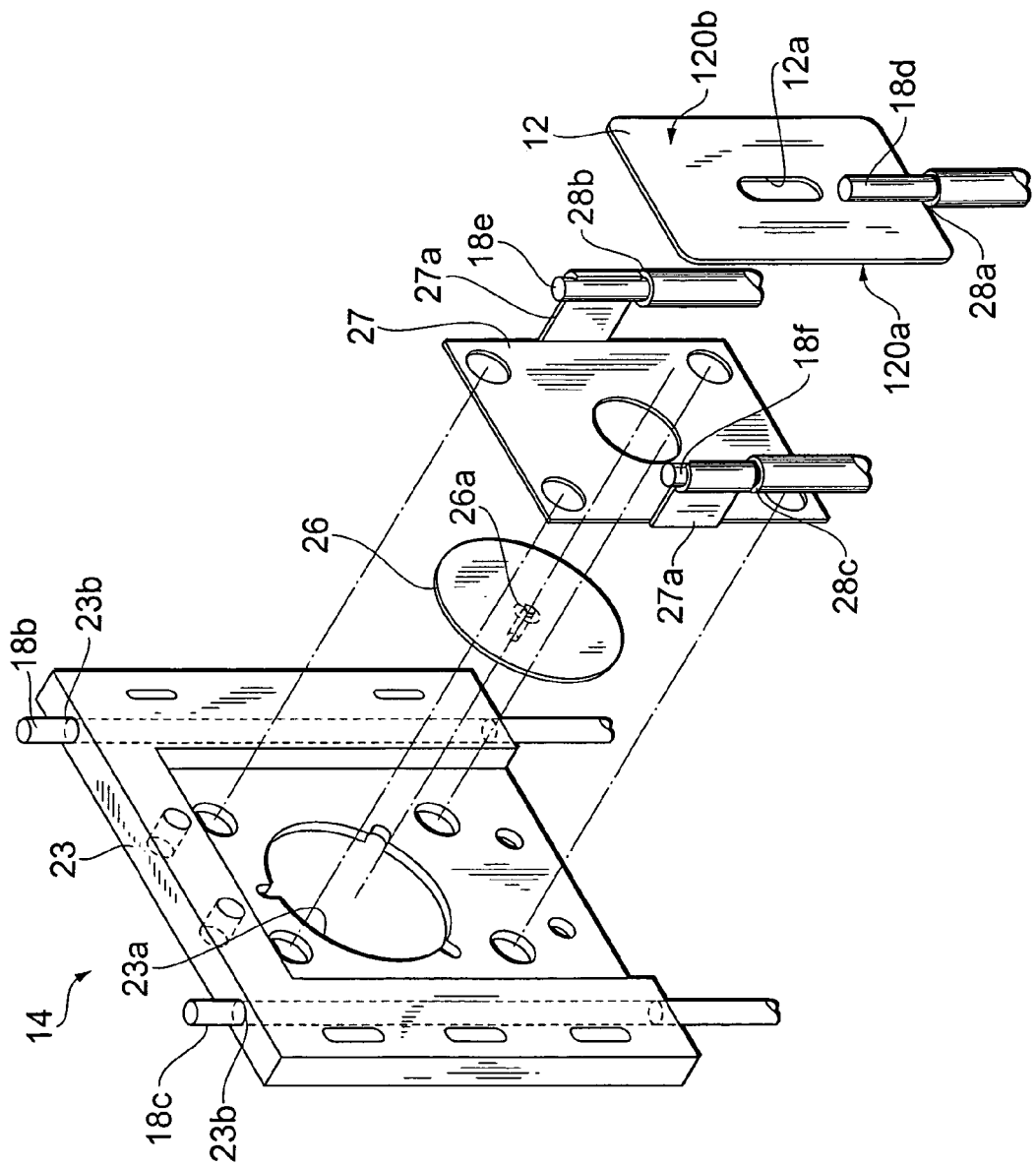
FIG. 5 is an exploded perspective view showing a supporting part, discharge path restricting section and anode section in a light-emitting part assembly shown in FIG. 4 from the rear side of the gas discharge tube.
Figure 6:
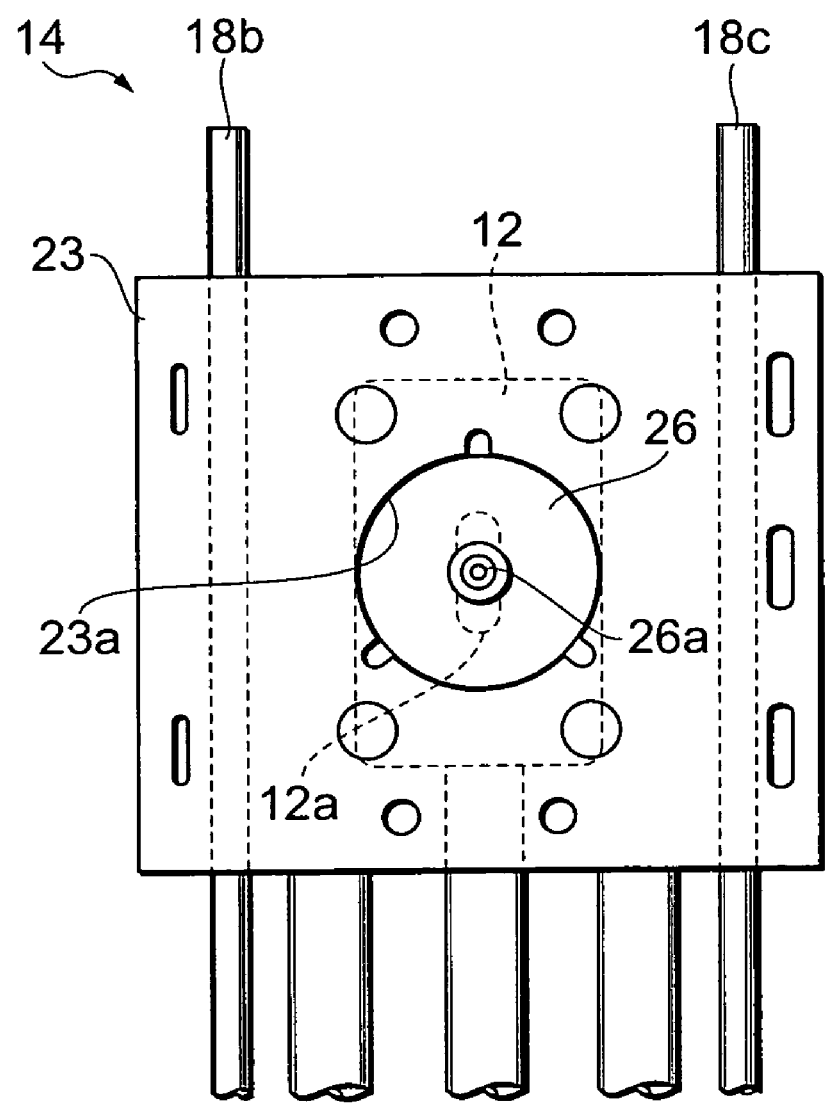
FIG. 6 is a front view of the supporting part, discharge path restricting section and anode section in the light-emitting part assembly shown in FIG. 4.

A plurality of conductive stem pins 18a to 18g (seven pins in this embodiment) are fixed to the stem part 16 in a state where the stem pins penetrate through the stem part 16 respectively. The stem pins 18a to 18g extend along the tube axial direction Y (the axial direction of the side tube: shown vertical direction). As shown in FIG. 5, level differences 28a to 28c are formed on tip parts of the stem pins 18d to 18f. The level differences 28a to 28c are used for the alignment of the anode section 12 connected to the tip end parts of the stem pins 18d to 18f and arm parts 27a and 27a extending to the rearward of a conductive plate 27 to be described later in the tube axial direction Y.

The light-emitting part assembly 14 generates arc discharge and emits ultraviolet radiation. As shown in FIG. 4, the light-emitting part assembly 14 is composed by a supporting member 23 supporting a base member 22 in which a housing space 21 for housing the anode section 12 is formed and a discharge path restricting section 26, and a front cover 24 which is arranged at the front face side of the supporting member 23 and in which a light passage opening 24a through which the ultraviolet radiation passes is formed other than the cathode section 13 for generating thermoelectrons contributing to discharge and the anode section 12 receiving the thermoelectrons from this cathode section 13. The cathode section 13 is electrically connected to an external power supply via the stem pins 18a and 18c shown in FIG. 1.

The base member 22 and the supporting member 23 are made of an insulating material such as ceramics. As shown in FIGS. 4 and 5, the supporting member 23 is a plate member in which a recessed portion as a housing space 21 is formed at the rear side. An opening 23a is formed at the center of the recessed portion, and the discharge path restricting section 26 for restricting a discharge path between the cathode section 13 and the anode section 12 is arranged in the opening 23a. Openings 23b and 23b extending in the tube axial direction Y are formed in the supporting member 23, and the stem pins 18b and 18c are respectively inserted into the openings 23b and 23b.

The discharge path restricting section 26 is made of metal such as molybdenum, tungsten or the alloy thereof and has conductivity. The discharge path restricting section 26 has a cylindrical shape, and as shown in FIGS. 8 and 9, its through-hole has a discharge path narrowing hole (diameter: approximately 0.5 mm) 26a for narrowing the discharge path and a conical part 26b for arc ball formation. As shown in FIGS. 4 and 8, the conductive plate 27 is electrically connected to the rear surface of the discharge path restricting section 26. As shown in FIGS. 4 and 5, the conductive plate 27 is housed in the housing space 21 in a state where the conductive plate 27 is electrically connected to the stem pins 18e and 18f.

The base member 22 is a plate member fixed to the rear surface of the supporting member 23 and shown in FIG. 4. A recessed portion constituting the housing space 21 is formed at the front side. As shown in FIGS. 3 and 4, an opening 22a communicating with the rear surface side is formed at the center of the recessed portion. The opening 22a passes through light emitted from another light source arranged on the rearward of the gas discharge tube 10. As shown in FIG. 4, the opening 22a formed on the base member 22, an oblong opening 12a formed in the anode section 12, the discharge path narrowing hole 26a and conical part 26b formed in the discharge path restricting section 26, and the light passage opening 24a formed on the front cover 24 are arranged on the same axle.

As shown in FIGS. 4 to 7, the anode section 12 is a plate electrode having a first surface 120a facing the discharge path restricting section 26 and a second surface 120b opposed to the first surface. An opening portion for communicating between the first surface 120a and the second surface 120b is formed in the anode section 12, and the opening portion is arranged along the tube axial direction Y in a state where it is supported by the stem pin 18d. That is, the plate anode section 12 is arranged so as to be approximately orthogonal to the optical axis X of the light emitted from the gas discharge tube 10. The oblong opening 12a as the opening portion is formed at the center of the anode section 12 so that the long width D2 extends in the tube axial direction Y. The cross-sectional shape on a surface perpendicular to the optical axis X of the oblong opening 12a is uniform along the direction of the optical axis X. Hereinafter, as shown in FIG. 10, the shorter opening width (opening width W1) of the oblong opening 12a is set to a short width D1, and the longer opening width (opening length L1) orthogonal to the short width D1 is referred to as a long width D2. Herein, the length of the short width D1 is approximately coincident with the diameter of the conventional circular opening, and the length of the long width D2 is longer than the diameter of the conventional circular opening. The short width D1 and the long width D2 exist on a surface perpendicular to the optical axis X, and intersect orthogonally with each other. The oblong opening 12a is obtained by forming linear parts 12c and 12c parallel with each other along the direction of the opening length L1 in the edge part (specifying the oblong opening 12a) of the anode section 12. At this time, edge parts 12d and 12d connecting the end parts of the linear parts 12c and 12c are processed into an arc shape having top parts 12e and 12e protruding to the outside.

Next, the alignment of the oblong opening 12a of the anode section 12 and discharge path narrowing hole 26a of the discharge path restricting section 26 will be explained with reference to FIG. 5 and FIGS. 7 to 10. First, as shown in FIGS. 5 and 8, the conductive plate 27 is fixed to the rear surface of the discharge path restricting section 26. Then, as shown in FIGS. 5 and 7, the conductive plate 27 is fixed to the supporting member 23 in a state where the discharge path restricting section 26 is arranged at the opening 23a of the supporting member 23. On the other hand, the anode section 12 is fixed to the tip of the stem pin 18d in a state where the lower end of the anode section 12 is abutted against the level difference 28a so that the oblong opening 12a extends along the tube axial direction Y.

Next, the stem pins 18b and 18c are inserted into the openings 23b and 23b of the supporting member 23, and the stem pins 18e and 18f are abutted against the side surfaces of the arm parts 27a and 27a of the conductive plate 27 in a state where the lower ends of the arm parts 27a and 27a are abutted against the level differences 28b and 28c. The discharge path restricting section 26 and the conductive plate 27 are arranged at a predetermined position to the supporting member 23 so that the axial center of the discharge path narrowing hole 26a is positioned almost on the same axis as that of the oblong opening 12a. A distance D3 between the discharge path restricting section 26 and anode section 12 shown in FIG. 9 is approximately 1 mm. Herein, even when the displacement of the oblong opening 12a is generated in the tube axial direction Y, there is no problem if the discharge path narrowing hole 26a is set to a position where it overlaps with the oblong opening 12a in the rear view (front view). That is, the displacement of the tube axial direction Y is tolerated by the shape of the oblong opening 12a. Reference numeral 12a shown by a virtual line in FIG. 10 designates a range R having no problem even when the displacement of the oblong opening 12a is generated in the tube axial direction Y.

Next, the operation of the gas discharge tube 10 having the above structure will be explained. First, electric power of approximately 10 W is supplied to the cathode section 13 via the stem pins 18a and 18c from an external power supply for cathode for approximately 20 seconds before discharge. Thereby, a coil constituting the cathode section 13 is previously heated. A voltage of approximately 160V is then applied via the stem pin 18d from a main discharge external power supply between the cathode section 13 and the anode section 12, and the preparation of arc discharge is completed.

A prescribed voltage, for example, a voltage of approximately 350V is then applied between the discharge path restricting section 26 and the anode section 12 via the stem pins 18d to 18f from a trigger external power supply. Then, starting discharge is generated between the cathode section 13 and the anode section 12, and the main discharge (arc discharge) is generated by the main discharge external power supply. Thus, the ultraviolet radiation is emitted through the light emitting window 17 by the generation of the main discharge.

Herein, as described above, one width D1 is shorter than the other width D2 among two widths D1 and D2 orthogonal to each other in the anode section 12 in the gas discharge tube 10 according to the embodiment. Therefore, the width D2 is made larger than the diameter of the conventional circular opening, and the width D1 can also be made coincident with the diameter of the conventional circular opening. Thus, the amount of the visible light from the visible light source passing through the oblong opening 12a of the anode section 12 of the gas discharge tube 10 can be increased by making the width D2 larger than the diameter of the conventional circular opening. On the other hand, both the maintenance of the discharge startability and the prevention of the shortening of the life of the anode section 12 can be realized by setting the width D1 to the same degree as the diameter of the conventional circular opening portion.

Since the anode section 12 has the oblong opening 12a, the increase of the opening area can be suppressed and the opening width of the predetermined direction can be made larger than the diameter of the conventional circular opening. Thereby, as compared with the case where the opening area of the conventional circular opening is simply enlarged, the discharge startability is improved by the increase of the current capacity. Since the thermal capacity of the anode section 12 is also increased in the same comparison, the life characteristic of the anode section 12 is also improved. On the other hand, since the opening width of the predetermined direction is increased, the amount of the passing through visible light can be increased.

The gas discharge tube 10 is a side-on type gas discharge tube for emitting light in a direction orthogonal to the tube axial direction Y of the sealed vessel 11. Therefore, the oblong opening 12a of the anode section 12 is formed so that the long width D2 extends along the tube axial direction Y. Therefore, there is no problem even when the oblong opening 12 is disposed in a state where the oblong opening 12 is misaligned to some degree in the tube axial direction Y to the discharge path narrowing hole 26a of the discharge path restricting section 26. On the contrary, the oblong opening 12a and discharge path restricting section 16 are easily positioned, and the assembly efficiency of the light-emitting part assembly 14 can be enhanced.

Figure 11:
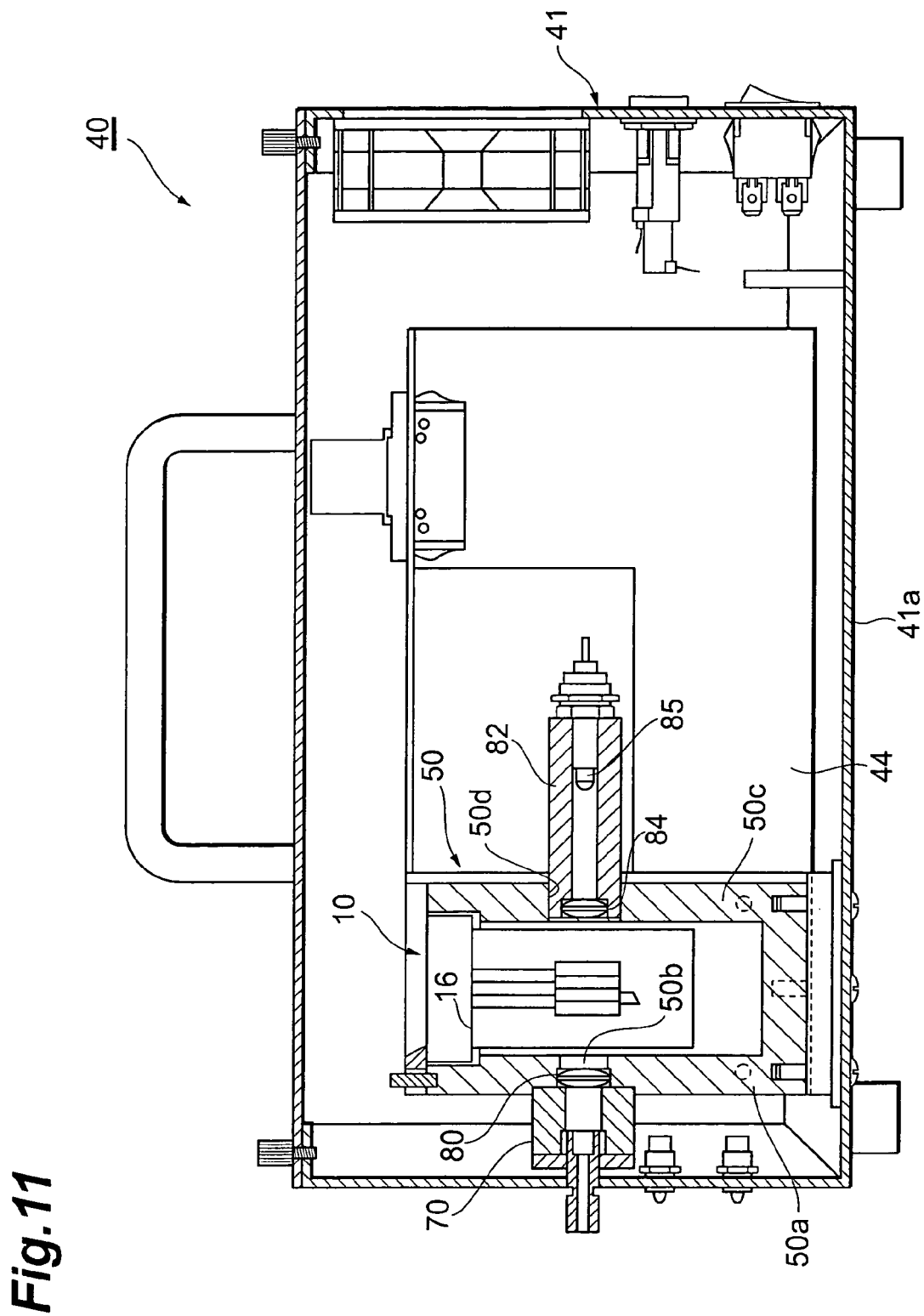
FIG. 11 is a sectional view showing the structure of an embodiment of a light source apparatus according to the present invention.

Next, a light source apparatus 40 comprising the gas discharge tube 10 having the above structure will be explained. As shown in FIG. 11, the light source apparatus 40 is a portable type light source apparatus constituting extreme lightness in weight and compactness, and being convenient for carrying. The light source apparatus 40 has a casing 41 having a shape of an approximate rectangular parallelepiped and made of steel. The gas discharge tube 10, a tungsten lamp 85 arranged at the rear surface side (shown right side) of the gas discharge tube 10 and emitting the visible light, and a power supply 44 for supplying electric power to the gas discharge tube 10 and the tungsten lamp 85 are housed in the casing 41.

The gas discharge tube 10 is housed in a lamp box 50 made of aluminum. The lamp box 50 is arranged at the front part side (shown left side) of the casing 41, and screwed to a bottom plate 41a of the casing 41. The gas discharge tube 10 is arranged so that the stem part 16 thereof is located above.

An opening 50b for passing through emitted light is formed at a position corresponding to the light passage opening 24a (see FIG. 2) of the gas discharge tube 10 on a front wall 50a of the front surface side of the lamp box 50. A condenser lens 80 is arranged at the opening 50b. A cylindrical light guiding cylinder 70 for passing through emitted light is provided at a position corresponding to the opening 50b at the front surface of the front wall 50a, and the light guiding cylinder 70 extends forward. The ultraviolet radiation emitted from the gas discharge tube 10 passes through the condenser lens 80, and is emitted out of the casing 41.

An opening 50d is formed at a position corresponding to the opening 22a (see FIG. 3) of the gas discharge tube 10 on a rear wall 50c of the rear surface side of the lamp box 50. A lamp housing pipe 82 extending rearward and housing the tungsten lamp 85 is inserted into the opening 50d. The tungsten lamp 85 is arranged at the rear end part of the lamp housing pipe 82, and a condenser lens 84 is arranged at the front end part of the lamp housing pipe 82. The visible light emitted from the tungsten lamp 85 passes through the condenser lens 84, the gas discharge tube 10 and the condenser lens 80 sequentially, is propagated in the same path as that of the ultraviolet radiation emitted from the gas discharge tube 10, and is emitted out of the casing 41.

Since the light source apparatus 40 having the structure has the gas discharge tube 10 and the tungsten lamp 85, the ultraviolet radiation from the gas discharge tube 10, the visible light from the tungsten lamp 85 and the emitted light of the combination thereof can be generated. Since the see-through type gas discharge tube 10 is applied, the optical system can be omitted, and the down-sized light source apparatus 40 can be realized.

Since the oblong opening 12a is formed in the anode section 12 of the gas discharge tube 10 even in the above light source apparatus 40, both the maintenance of the discharge startability and the prevention of the shortening of the life of the anode section can be realized, and the amount of the visible light from the visible light source passing through the gas discharge tube 10 can be increased. As a result, the amount of the light emitted from the entire light source apparatus 40 can be increased.

Though the light source apparatus 40 includes the tungsten lamp 85 as the visible light source, the light source apparatus 40 may includes another visible light source including a halogen lamp.

Figure 12:
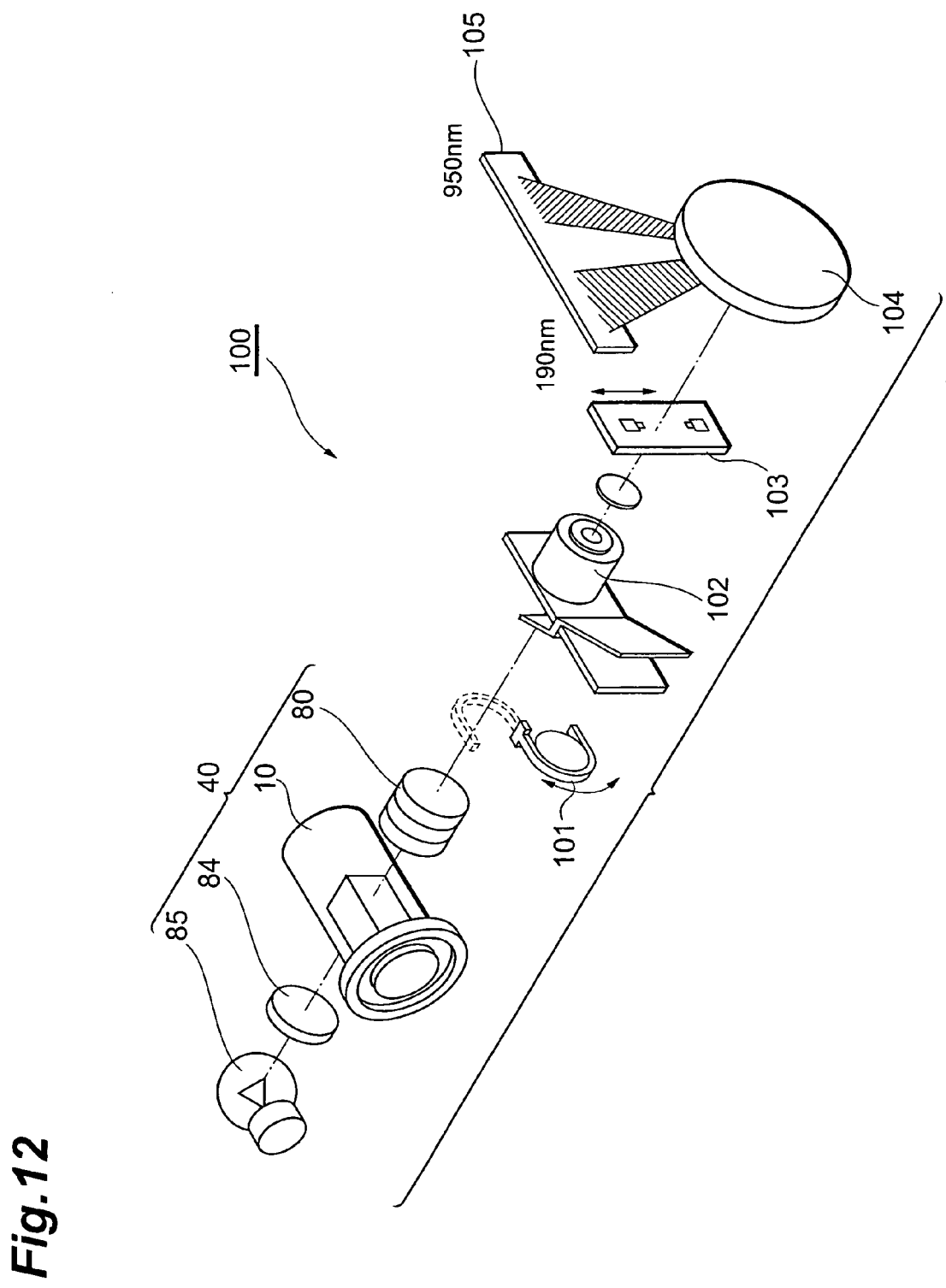
FIG. 12 is a schematic view showing the structure of an embodiment of a liquid chromatograph according to the present invention.

Next, a liquid chromatograph 100 comprising the light source apparatus 40 having the above structure will be explained. For example, the liquid chromatograph 100 is an ultraviolet visible light absorption detector used for the analysis of an organic compound or the like. As shown in FIG. 12, in addition to the above-described gas discharge tube 10 and the light source apparatus 40 having the tungsten lamp 85, the liquid chromatograph 100 comprises a holomium oxide filter 101 for optimizing the wavelength of the light emitted from the light source apparatus 40, a cell 102 on which an object to be analyzed is loaded, a slit 103 for diffracting light transmitted through the cell 102, a grating 104 separating the light diffracted by the slit 103, and a photodiode 105 for detecting the light separated by the grating 104. The slit 103 is controlled by a program and can optimize spectral resolution performance and sensitivity. The photodiode 105 is arranged in an array, and can detect a plurality of wavelengths simultaneously. Since the liquid chromatograph 100 can measure in a wider wavelength range (190 nm to 950 nm) as compared with the conventional liquid chromatograph, highly reliable analysis can be performed.

Since the liquid chromatograph 100 also comprises the gas discharge tube 10 having the above structure, both the maintenance of the discharge startability and the prevention of the shortening of the life of the anode section can be realized, and the amount of the visible light from the visible light source passing through the gas discharge tube 10 can be increased.

Figure 13:
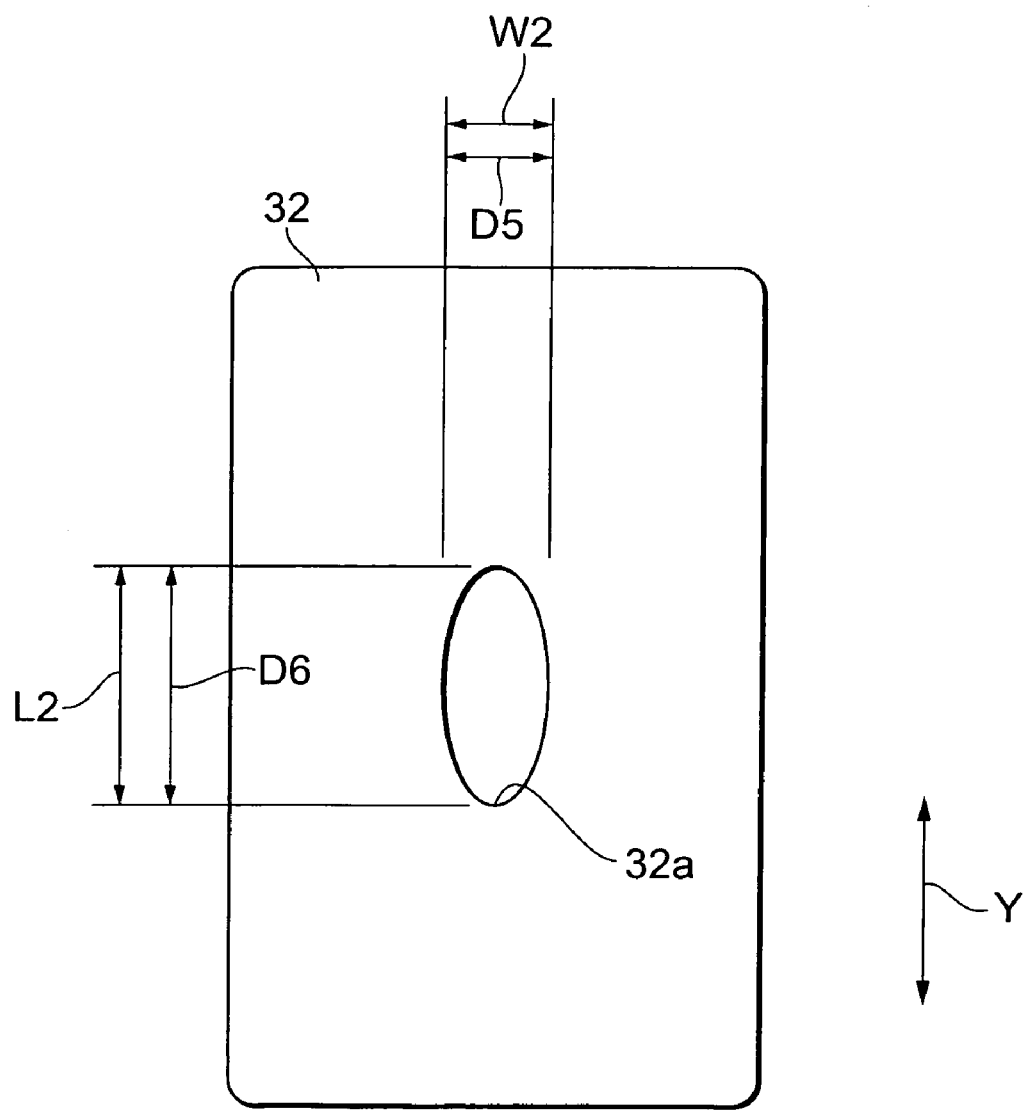
FIG. 13 is a front view showing another structure of an anode section which is applicable to a gas discharge tube according to the present invention.

Next, another structure of the anode section which is applicable to the gas discharge tube according to the present invention will be explained referring to FIG. 13. The gas discharge tube of the embodiment is different from the gas discharge tube shown in FIGS. 1 to 4 in that the shape of the opening portion formed in the anode section is changed. Specifically, instead of the above anode section 12 in which the oblong opening 12a is formed, an anode section 32 in which an elliptic opening 32a is formed is applied. The anode section 32 is also a plate electrode having a first surface and second surface mutually opposed as in the above anode section 12. A shorter width (opening width W2) of the elliptic opening 32a is set to a short width D5, and a longer width (opening length L2) orthogonal to the short width D5 is set to a long width D6. The length of the short width D5 is approximately coincident with the diameter of the conventional circular opening portion, and the length of the long width D6 is longer than the diameter of the conventional circular opening. Herein, the short width D5 and the long width D6 intersect orthogonally with each other on an opening section perpendicular to the optical axis X. The structure also exhibits the same action and effect as those of the gas discharge tube 10 shown in FIGS. 1 to 4.

Figure 14:
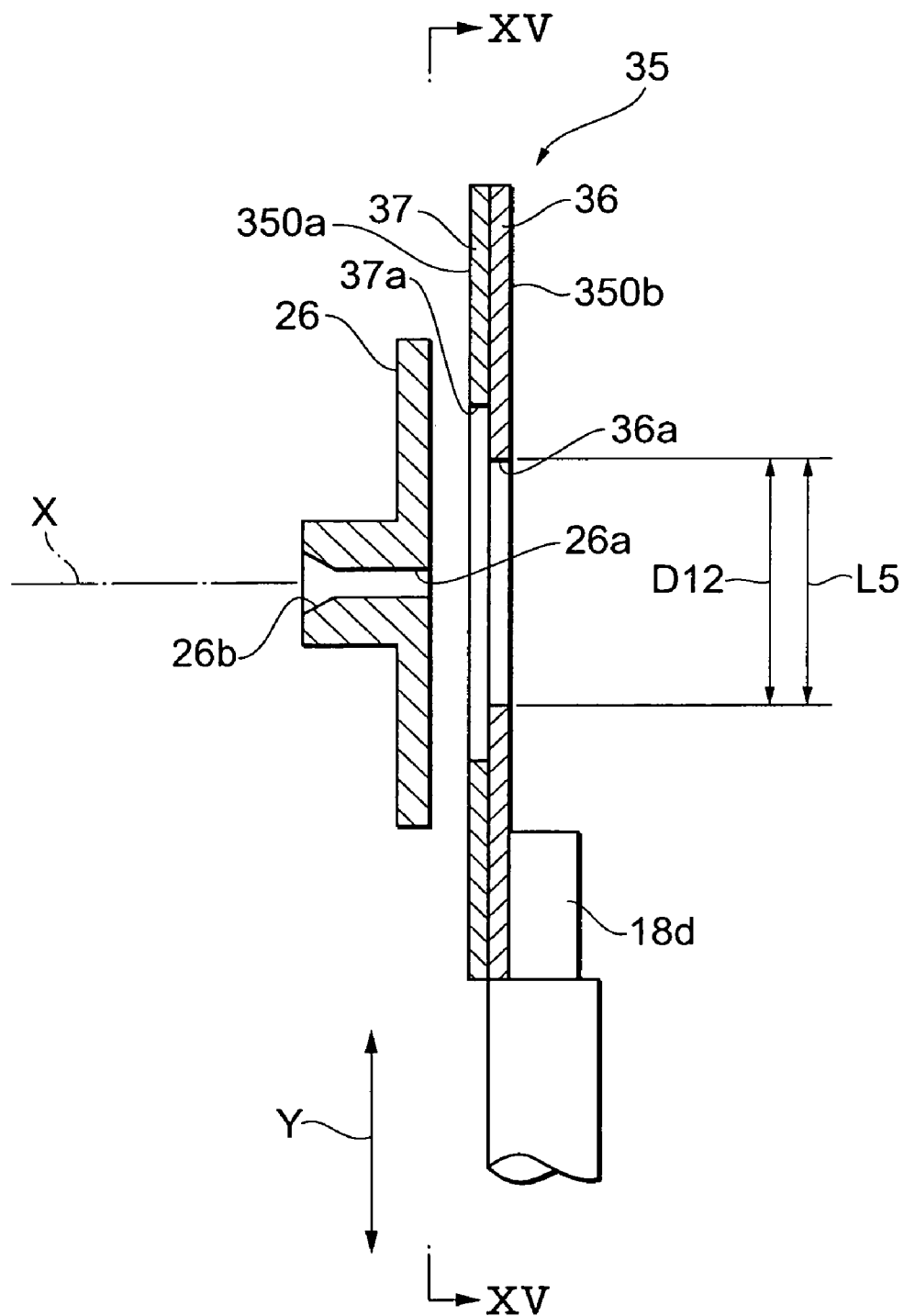
FIG. 14 is a sectional view showing another positional relationship between the discharge path narrowing hole and anode section in the gas discharge tube according to the present invention.
Figure 15:
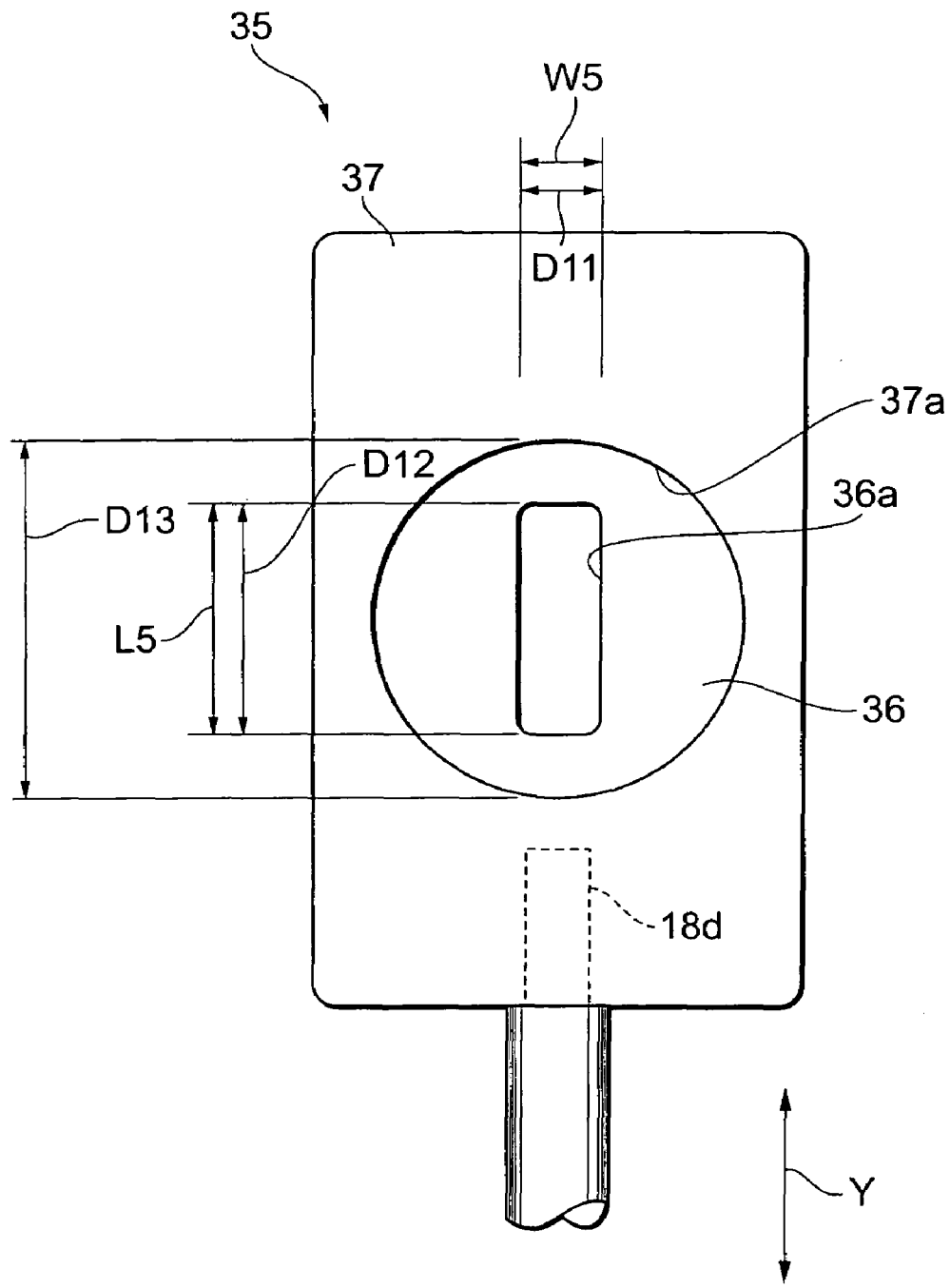
FIG. 15 is a front view of the anode section shown in FIG. 14.

Furthermore, a gas discharge tube according to another embodiment of the present invention will be explained referring to FIGS. 14 and 15. FIG. 15 is a front view of an anode section 35 viewed in a direction of an arrow from a position of the XV-XV line in FIG. 14. The gas discharge tube according to the embodiment is different from the gas discharge tube shown in FIGS. 1 to 4 in that an anode section 35 having opening portions 36a and 37a formed with different opening shapes along the direction of the optical axis X is applied instead of the anode section 12 having the opening 12a for which the opening shape is not changed along the direction of the optical axis X (the direction of a plate thickness). The anode section 35 is constituted by a two-plate-bonded material. Same as the above-mentioned anode section 12, the anode section 35 also has a first surface 350a facing the discharge path restricting section 26 and a second surface 350b opposed to the first surface 350a. A plate material of the rear surface side of two-plate material constitutes an anode section body 36, and a plate material of the front surface side constitutes an anode section front plate 37. The anode section body 36 extends in the tube axial direction Y in a state where the anode section body 36 is supported by the stem pin 18d. Herein, the anode section 35 is arranged so as to be orthogonal to the optical axis X of the gas discharge tube, and a rectangular opening 36a of which the long width D12 extends in the tube axial direction Y is formed at the center of the anode section body 36. A shorter width (opening width W5) of the rectangular opening 36a is set to a short width D11, and a longer width (opening length L5) orthogonal to the short width D11 is set to a long width D12. The length of the short width D11 is approximately the same as the diameter of the conventional circular opening, and the length of the long width D12 is longer than the diameter of the conventional circular opening. Herein, the short width D11 and the long width D12 intersect orthogonally with each other on the opening section perpendicular to the optical axis X. On the other hand, a circular opening portion 37a is formed at the center of the anode section front plate 37. The circular opening portion 37a is arranged so as to be coaxial with the rectangular opening portion 36a. The diameter D13 of the circular opening portion 37a is set to be longer than the long width D12 of the rectangular opening 36a.

Figure 16:
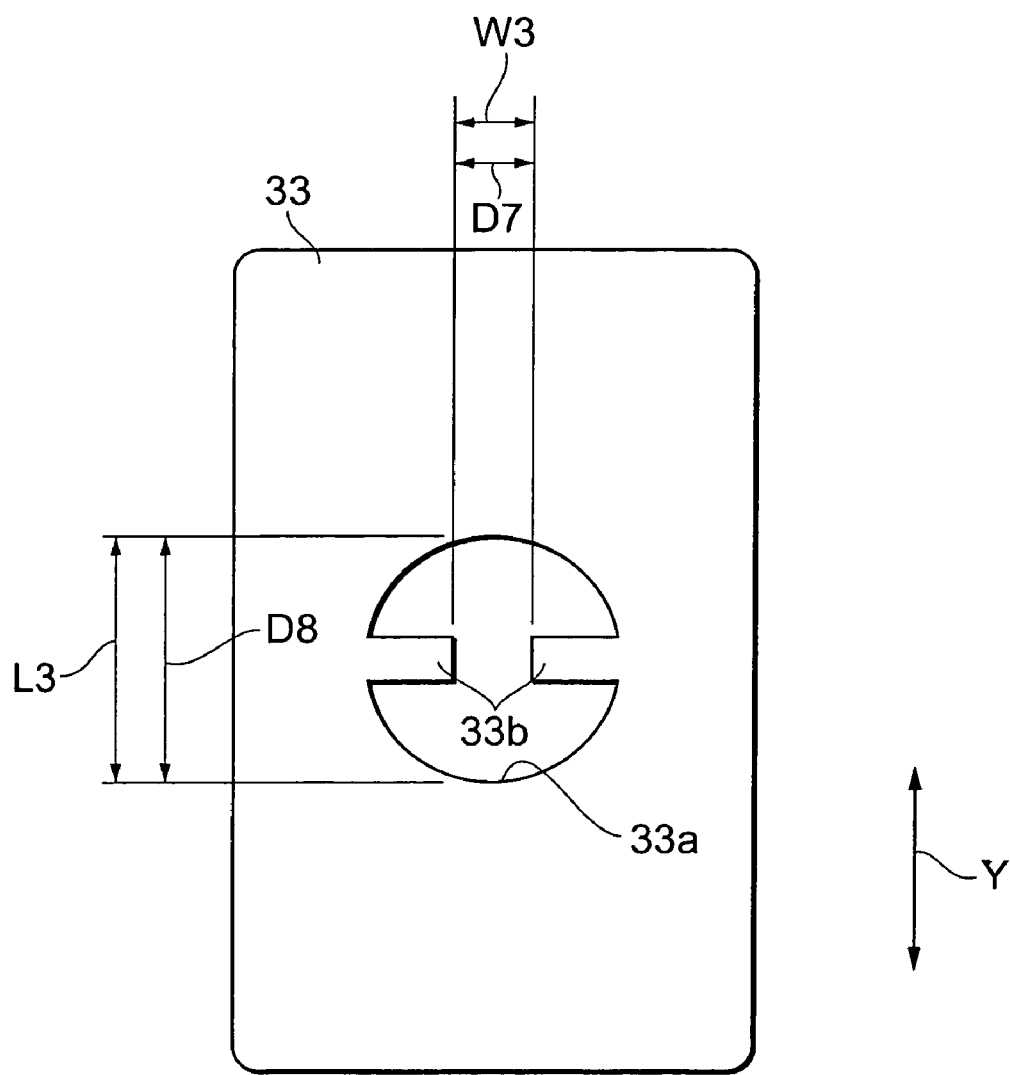
FIG. 16 is a front view showing another structure of the anode section which is applicable to the gas discharge tube according to the present invention.
Figure 17:
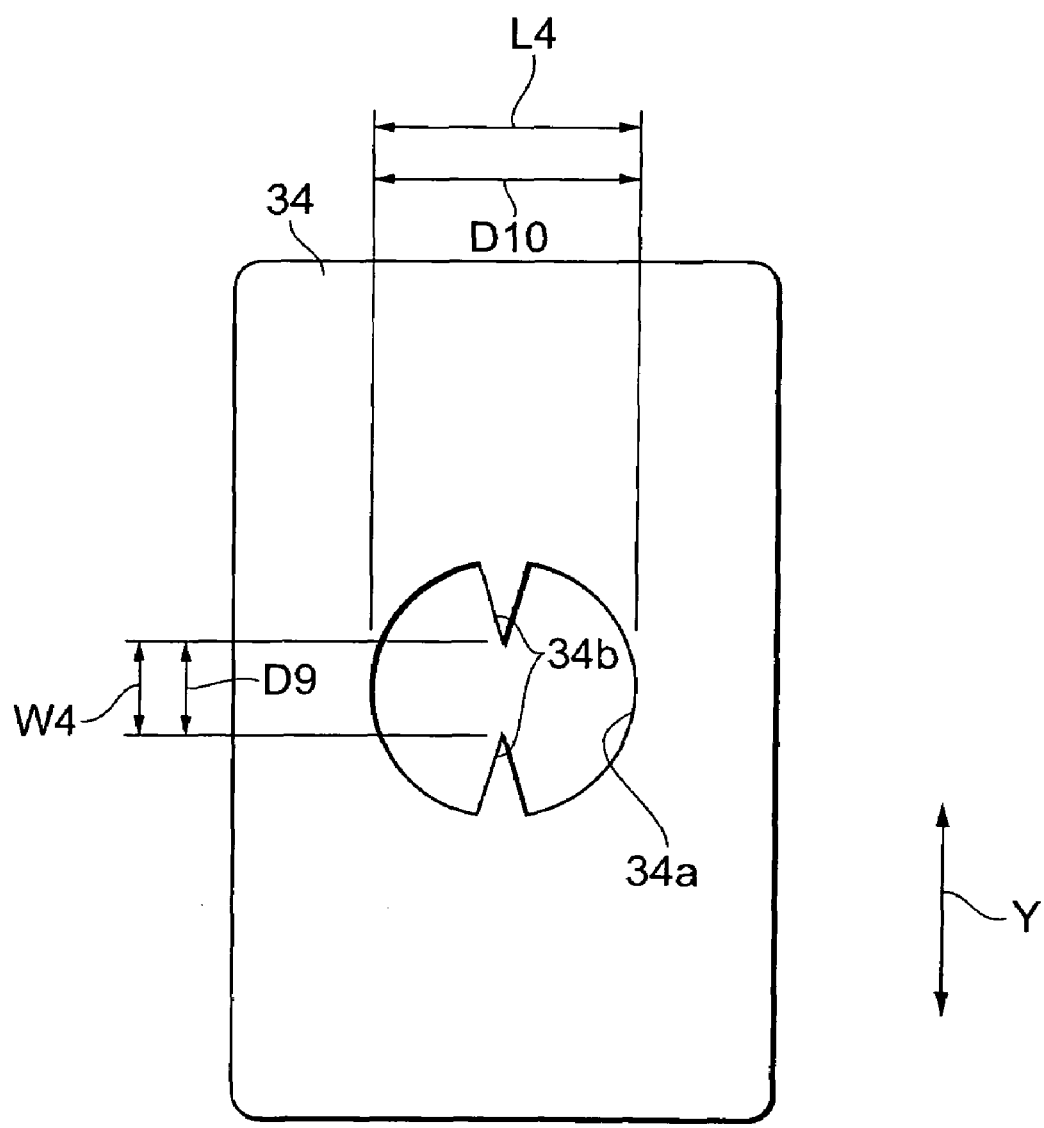
FIG. 17 is a front view showing another structure of the anode section which is applicable to the gas discharge tube according to the present invention.

As described above, though the present invention is specifically explained based on various embodiments, the present invention is not limited to the above embodiments. Specifically, though the above embodiments disclose the gas discharge tube 10 having the anode sections 12, 32, and 35 in which the oblong opening 12a, the elliptic opening 32a and the rectangular opening 36a are formed as the opening portion, the opening portion formed in the anode section is not limited to the above oblong opening 12a, elliptic opening 32a and rectangular opening 36a. For example, as shown in FIG. 16, in an anode section 33, an opening portion 33a having the short width (opening width W3) D7 and the long width (opening length L3) D8 may be formed as the opening portion. In the anode section 33, a rectangular convex parts 33b and 33b protruding toward the axial center from the both sides of a direction orthogonal to the tube axial direction Y to the circular (the length of the diameter is the same as that of the long diameter D8) opening edge part are formed, and thereby the opening portion 33a having the short width D7 is formed (the short width D7 is smaller than the long width D8). As shown in FIG. 17, an opening portion 34a having a short width (opening width W4) D9 and a long width (opening length L4) D10 may be formed in an anode section 34. In the anode section 34, mountain-shaped convex parts 34b and 34b protruding toward the axial center from the both sides of the tube axial direction Y to the circular (the diameter has the same length as that of the long width D10) opening edge part are formed, and the opening portion 34a having the short width D9 is formed (the short width D9 is smaller than the long width D10).

Even in the anode section shown in FIGS. 16 and 17, the amount of the visible light from the visible light source passing through the discharge narrowing hole without reducing the discharge startability can be increased as compared with the case where the opening area of the conventional circular opening is simply enlarged. Particularly, according to the anode sections 12, 32, and 35, the oblong opening (see FIG. 10) 12a, the elliptic opening (see FIG. 13) 32a and the rectangular opening (see FIG. 15) 36a are formed as described above. Therefore, since the edge part in the anode section constituting the short width (one width) of the openings 12a, 32a, and 36a extends in the long width (another width) direction, the discharge is dispersed, and the discharge startability can be well maintained. In this regard, the anode sections 12, 32, and 35 are superior to the anode sections 33 and 34 shown in FIGS. 14 and 15.

Though the above explanation relates to the side-on type gas discharge tube 10, a head-on type gas discharge tube may be used. An optical system for guiding the visible light from the visible light source to the opening portion of the anode section is required when the stem part is interposed between the opening portion of the anode section and the visible light source in the case of the head-on type.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

INDUSTRIAL APPLICABILITY

The gas discharge tube according to the present invention can be suitably applied to light sources such as the liquid chromatograph and the semiconductor inspection device.

The invention claimed is:
1. A gas discharge tube comprising:
a sealed vessel in which gas is encapsulated;
a cathode section arranged in said sealed vessel;
an anode section, arranged in said sealed vessel, for generating discharge between said anode section and said cathode section; and
a discharge path restricting section, arranged in said sealed vessel, having a single hole for narrowing a discharge path between said cathode section and said anode section,
wherein said anode section has a first surface facing said discharge path restricting section, a second surface opposing said first surface, and a single opening portion for communicating between said first surface and said second surface, said single opening portion provided so as to correspond one-to-one with said single hole of said discharge path restricting section,
wherein a cross section of said single opening portion defined on a first reference plane coincident with said first surface has a non-circular shape, and
wherein said entire single hole is included in said single opening portion, when viewing said single hole through said single opening portion along an optical axis of light to be emitted from said gas discharge tube.

2. A gas discharge tube according to claim 1, wherein the cross section of said single opening portion has a non-circular shape where the maximum opening width in a first direction is different from that in a second direction orthogonal to the first direction.

3. A gas discharge tube according to claim 1, wherein the cross section of said single opening portion has one of an elliptic shape, an oblong shape and a rectangular shape.

4. A gas discharge tube according to claim 1, wherein the opening width of a part of said single opening portion is adjusted by a projection extending along the first reference plane from an edge part of said anode section defining said single opening portion.

5. A gas discharge tube according to claim 2, wherein the maximum opening width in the second direction of the cross section of said single opening portion is adjusted by a projection extending in the second direction from an edge part of said anode section defining said single opening portion.

6. A gas discharge tube according to claim 1, wherein said anode section is arranged such that said first surface is parallel to a tube axial direction of said sealed vessel so as to emit light in a direction orthogonal to the tube axial direction of said sealed vessel.

7. A light source apparatus comprising:
a gas discharge tube of claim 1; and
a visible light source for emitting visible light toward said single opening portion of said anode section constituting a part of said gas discharge tube.

8. A liquid chromatograph including a light source apparatus according to claim 7.

9. A gas discharge tube according to claim 1, wherein a maximum opening width of said single opening portion defined on the first reference plane coincident with said first surface is larger than the maximum opening width of said single opening portion defined on a second reference plane coincident with said second surface.

10. A gas discharge tube according to claim 1, wherein said anode is supported by a stem pin extending from a bottom surface of said sealed vessel, and, on said first reference plane coincident with said first surface, a cross section of said single opening portion has a shape such that a long axis of said single opening portion, defined by a maximum width of said single opening portion, is in parallel with a longitudinal direction of said stem pin.

* * * * *